(12) United States Patent
Emrick et al.

(10) Patent No.: US 9,388,273 B2
(45) Date of Patent: Jul. 12, 2016

(54) MULTIFUNCTIONAL DEOXYBENZOIN-BASED MONOMERS AND RESINS HAVING REDUCED FLAMMABILITY

(71) Applicant: University of Massachusetts, Boston, MA (US)

(72) Inventors: Todd Emrick, South Deerfield, MA (US); Justin Timmons, Agawam, MA (US); Megan Warner Szyndler, Amherst, MA (US)

(73) Assignee: University of Massachusetts, Boston, MA (US)

( * ) Notice: Subject to any disclaimer, the term of this patent is extended or adjusted under 35 U.S.C. 154(b) by 84 days.

(21) Appl. No.: 14/280,901

(22) Filed: May 19, 2014

(65) Prior Publication Data
US 2014/0357829 A1 Dec. 4, 2014

Related U.S. Application Data

(60) Provisional application No. 61/824,476, filed on May 17, 2013.

(51) Int. Cl.
| | |
|---|---|
| *C07C 39/14* | (2006.01) |
| *C07C 39/15* | (2006.01) |
| *C07C 303/28* | (2006.01) |
| *C07C 303/30* | (2006.01) |
| *C08G 59/06* | (2006.01) |
| *C08G 65/38* | (2006.01) |
| *C08G 59/32* | (2006.01) |
| *C07D 303/30* | (2006.01) |
| *C07C 49/83* | (2006.01) |
| *C07D 303/28* | (2006.01) |
| *C08G 65/40* | (2006.01) |

(52) U.S. Cl.
CPC ............ *C08G 59/3218* (2013.01); *C07C 39/14* (2013.01); *C07C 39/15* (2013.01); *C07C 49/83* (2013.01); *C07D 303/28* (2013.01); *C07D 303/30* (2013.01); *C08G 59/063* (2013.01); *C08G 65/4012* (2013.01)

(58) Field of Classification Search
None
See application file for complete search history.

(56) References Cited

U.S. PATENT DOCUMENTS

2005/0004400 A1* 1/2005 Haremza ................ C07C 45/00
568/309

FOREIGN PATENT DOCUMENTS

| WO | WO 2009/123969 A2 * | 10/2009 | ............ C08G 18/10 |
| WO | WO 2012/151154 A2 * | 11/2012 | ............ C07C 49/83 |

OTHER PUBLICATIONS

Publication No. CN001785971A and Derwent accession No. 2007-102654 for Chinese Patent No. 1785971 A, Yan et al., Jun. 14, 2006, two pages.*
PubChem CHEMBL243376 for 2,3,4,4'-tetrahydroxydeoxybenzoin, Feb. 9, 2007, pp. 1-11.*
HCAPLUS accession No. 2003:467313 for U.S. Publication No. 2005/0004400, Haremza, Jun. 18, 2003, 3 pages.*
Journal of Materials Chemistry, Ranganathan et al., vol. 20, Issue 18, 2010, pp. 3681-3687.*
Journal of Polymer Science: Polymer Chemistry, Ranganathan et al., vol. 45, Issue 20, 2007, pp. 4573-4580.*
Macromolecules, Ellzey et al., vol. 39, Issue 10, 2006, pp. 3553-3558.*
Macromolecules, Ranganathan et al., vol. 39, Issue 18, 2006, pp. 5974-5975.*
Macromolecules, Ryu et al., vol. 44, Issue 14, 2011, pp. 5693-5700.*
Polymer, Ryu et al., vol. 50, Issue 3, 2009, pp. 767-774.*

* cited by examiner

*Primary Examiner* — Robert Sellers
(74) *Attorney, Agent, or Firm* — Milstein Zhang & Wu LLC (57) ABSTRACT

The invention provides a novel platform for minimal- or non-flammable polymers, which is based purely on hydrocarbon systems and does not need additives of any kind A key feature is that the hydrocarbons disclosed herein are characterized by degradation mechanisms that produce few flammable volatiles. For example, 2,4,4',6-tetrahydroxydeoxybenzoin is employed as a multifunctional cross-linker in conjunction with bis-epoxydeoxybenzoin, affording new resins that combine excellent physical and mechanical properties with low flammability.

18 Claims, 5 Drawing Sheets

MULTIFUNCTIONAL DEOXYBENZOIN-BASED MONOMERS AND RESINS HAVING REDUCED FLAMMABILITY

PRIORITY CLAIMS AND RELATED APPLICATIONS

This application claims the benefit of U.S. Provisional Application No. 61/824,476, filed May 17, 2013, the entire content of which is incorporated herein by reference in its entirety.

GOVERNMENT RIGHTS

The United States Government has certain rights to the invention pursuant to Grant No. 09-G-013 from Federal Aviation Administration and Grant No. W911QY-09-1-002 from the Army to the University of Massachusetts.

TECHNICAL FIELD OF THE INVENTION

The invention relates to flame retardant polymers. More particularly, the invention relates to cross-linked, deoxybenzoin-based resins, and related methods and uses thereof.

BACKGROUND OF THE INVENTION

Polymers are a mainstay of modern society, for example, widely used in fabricating textiles, upholstery, construction materials, various air, land or sea vehicles, and microelectronic devices and appliances. The inherent flammability of many polymers poses a significant threat, especially in enclosed or isolated spaces. Therefore, as synthetic polymers are used extensively in society as plastics, rubbers, and textiles, polymer flammability has been recognized as a safety hazard and remains an important challenge in polymer research.

Epoxy resins are prominent among thermoset polymers, employed as high performance adhesives, surface coatings, encapsulation matrices, and composites in applications ranging from aerospace transportation to microelectronics packaging. (Odian G. 2004 Principles of Polymerization, Fourth ed. Hoboken, N.J.: John Wiley & Sons, Inc.; Hergenrother, et al. 2005 *Polymer* 46(14):5012-5024; Rakotomalala, et al. 2010 *Materials* 3(8):4300-4327.) Epoxy resins, like many synthetic polymer materials, require low flammability for their safe use. While halogenated flame retardants (FR) are common additives that impart low flammability to materials, there is a growing concern over the potential health and environmental consequences of such additives. Halogenated flame retardants are known to release undesirable hydrogen halide gas upon combustion.

With respect to epoxy resins, efforts towards non-halogenated materials center on the integration of phosphorus, boron, or silicon into the cross-linked matrix. (Hergenrother, et al. 2005 *Polymer* 46(14):5012-5024; Rakotomalala, et al. 2010 *Materials* 3(8):4300-4327; Lu, et al. 2002 *Prog Polym Sci* 27(8):1661-1712; Levchik, et al. 2005 *Polym Degrad Stabil* 88(1):57-62; Lv, et al. 2013 *Ind Eng Chem Res* 52(27): 9397-9404; Mauerer 2005 *Polym Degrad Stabil* 88(1):70-73; Toldy, et al. 2008 *Polym Degrad Stabil* 93(11):2007-2013; Weil, et al. 2004 *J Fire Sci* 22(1):25-40; Martin, et al. 2006 *J Polym Sci Pol Chem* 44(5):1701-1710; Martin, et al. 2006 *J Polym Sci Pol Chem* 44(21):6332-6344; Deng, et al. 2012 *Ind Eng Chem Res* 51(24):8178-8184; Devaraju, et al. 2013 *Polym Composite* 34(6):904-91 1; Gao, et al. 2013 *J Appl Polym Sci* 127(3):1842-1847.) However, non-halogenated flame retardant additives, such as alumina trihydrate, compromise the physical and mechanical properties of polymers when loaded at high levels.

Thus, there remains an urgent, on-going need for novel synthetic strategies toward a broad range of structurally and functionally diverse flame-retardant polymers.

SUMMARY OF THE INVENTION

The invention provides a novel platform for minimal- or non-flammable polymers, which is based purely on hydrocarbon systems and does not need additives of any kind A key feature is that the hydrocarbons disclosed herein are characterized by degradation mechanisms that produce few flammable volatiles. For example, 2,4,4',6-tetrahydroxydeoxybenzoin is employed as a multifunctional cross-linker in conjunction with bis-epoxydeoxybenzoin (BEDB), affording new resins that combine excellent physical and mechanical properties with low flammability. Exemplary resins fabricated from THDB exhibited low total heat release (13 kJ/g) and high char yields (34%), as well as excellent mechanical properties. The desirable heat release and char yield properties of these structures are realized without the need for any conventional flame retardant, such as halogenated structures or inorganic fillers that are commonly utilized in commercial materials.

In one aspect, the invention generally relates to a compound having the structural formula of:

wherein each R in $(OR)_i$ and $(OR)_j$ is independently selected from H and i is an integer selected from 1, 2, 3, 4 and 5; j is an integer selected from 1 and 2; and each of $R_1$ and $R_2$ is independently selected from H and $(C_1-C_6)$ alkyl groups.

In another aspect, the invention generally relates to a polymer prepared from a monomer having the structural formula of wherein each R in $(OR)_i$ and $(OR)_j$ is independently selected from H and i is an integer selected from 1, 2, 3, 4 and 5; j is an integer selected from 1 and 2; and each of $R_1$ and $R_2$ is independently selected from H and ($C_1$-$C_6$) alkyl groups.

In yet another embodiment, the invention generally relates to a minimal- or non-flammable composition, which includes a polymer comprising a monomer having the structural formula of wherein each R in (OR)$_i$ and (OR)$_j$ is independently selected from H and i is an integer selected from 1, 2, 3, 4 and 5; j is an integer selected from 1 and 2; and each of $R_1$ and $R_2$ is independently selected from H and ($C_1$-$C_6$) alkyl groups.

In certain embodiments, i is 2 or 3, j is 1. In certain embodiments, each of $R_1$ and $R_2$ is H. In certain preferred embodiments, the monomer has the structural formula of wherein each R independently is H or

In certain preferred embodiments, each R is H. In certain preferred embodiments, at least one R is In certain preferred embodiments, each R is

BRIEF DESCRIPTION OF THE DRAWINGS

FIG. 5. (a) Exemplary thermogravimetric analysis of ETHDB 1.8, 2.5 and 3.5; (b) Exemplary thermogravimetric analysis of desoxyanisoin, the diglycidyl ether of bisphenol A (DGEBA), BHDB, BEDB, and THDB.

DETAILED DESCRIPTION OF THE INVENTION

The invention provides a novel platform for minimal- or non-flammable resins, which is based purely on hydrocarbon systems and does not need additives of any kind The hydrocarbons disclosed herein are characterized by degradation mechanisms that produce few flammable volatiles. Importantly, these hydrocarbons possess suitable processability and performance characteristics. The multifunctional adhesive materials of the invention have low flammability, and related methods of preparation and uses there of. The low flammability is due to the structure of the organic/polymeric components used in the adhesive formulation, rather than through the addition of a conventional anti-flammable additive such as halogenated organic molecules or phosphorous-containing structures.

Research effort has been directed to low flammability high performance polymers that are prepared from deoxybenzoin-containing polymers. (Ryu, et al. 2011 *Macromolecules* 44(14):5693-5700; Ryu, et al. 2009 *Polymer* 50(3):767-774; Ellzey, et al. 2006 *Macromolecules* 39(10):3553-3558; Ranganathan, et al. 2010 *J Mater Chem* 20(18):3681-3687; Ranganathan, et al. 2007 *J Polym Sci Pol Chem* 45(20):4573-4580; Ranganathan, et al. 2006 *Macromolecules* 39(18):5974-5975.) Bis-hydroxydeoxybenzoin (BHDB) can function as a drop-in replacement for conventional bis-phenols, such as bisphenol A (BPA), including as cross-linked epoxides. For example, bis-epoxydeoxybenzoin (BEDB), though halogen-free, gives cross-linked polymer resins in conjunction with aromatic amines, affording robust adhesives with heat release capacity (HRC) values that are 20-40% lower than conventional BPA-based resins.

The present disclosure provides the preparation of an "all-deoxybenzoin" cross-linked resin. For example, one such all-deoxybenzoin cross-linked resin is comprised of tetrafunctional 2,4,4',6-tetrahydroxydeoxybenzoin (THDB), with BEDB as the epoxide component. Utilizing THDB, a novel tetraepoxydeoxybenzoin (TEDB) was synthesized. The char residue and heat release capacities were investigated by thermal gravimetric analysis (TGA) and pyrolysis combustion flow calorimetry (PCFC). TEDB and the lower epoxy-number derivatives were shown to exhibit low heat release and high char yield characteristics, as well as excellent mechanical properties, making them suitable for consideration in high performance adhesive materials. Importantly, the heat release and char yield properties from these novel compounds were realized without the presence of halogen in the structures.

Thus, the minimal- or non-flammable materials disclosed herein do not need to include halogen, phosphorous, or other conventional flame retardants or additives in the structure to achieve the desired performance characteristics. The invention enables the design and synthesis of hydrocarbons that have high char yield and low heat release and at the same time that possess suitable processibility characteristics. The approach disclosed herein is critical to achieve materials that lack the potential negative health, environmental, and materials aspects associated with conventional flame retardants.

Multi-functional deoxybenzoins, including THDB and its epoxy derivatives have been examined and the results are disclosed herein. The employed epoxidation conditions gave a mixture of products, with different numbers of epoxy groups per molecule. The product is herein defined as E-THDB-x, or the epoxy of THDB in which 'x' equals the epoxy number, or number of glycidyl ether groups per molecule (e.g., 1, 2, 3, 4).

Figure 1:
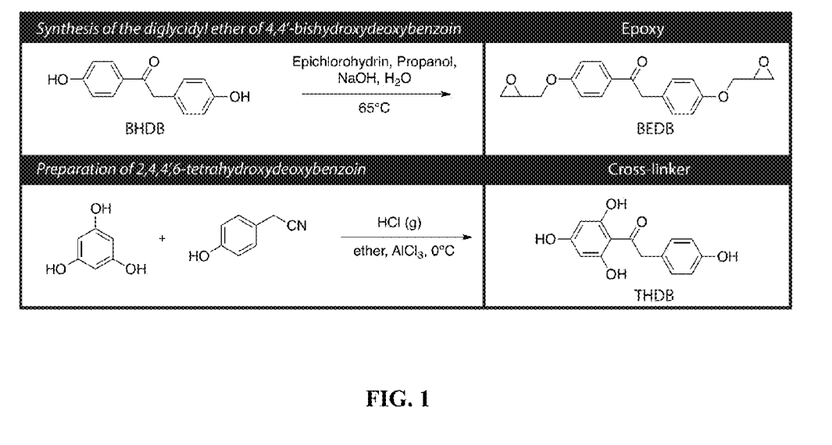
FIG. 1. Exemplary synthetic schemes for the synthesis of BEDB (top) and THDB (bottom).

BEDB was prepared by reacting BHDB with an excess of epichlorohydrin in an aqueous solution of sodium hydroxide, as shown in FIG. 1. The BEDB synthesis is scalable, and the diglycidyl ether is stable when stored in the laboratory under ambient conditions. THDB was synthesized under Houben-Hoesch conditions, as shown in FIG. 1, starting from phloroglucinol and 4-hydroxyphenylacetonitrile (Xiao, et al. 2007 *Bioorg Med Chem* 15(11):3703-3710; Chang, et al. 1994 *J Agr Food Chem* 42(9):1869-1871; Balasubramanian, et al. 2000 *Synthetic Commun* 30(3):469-484.) The THDB synthesis is scalable. Using THDB as a multifunctional phenol, and BEDB as the epoxy component, epoxy resins were generated in which the entirety of the polymer resin is composed of monomer units having the inherently non-flammable deoxybenzoin structure.

Figure 2:
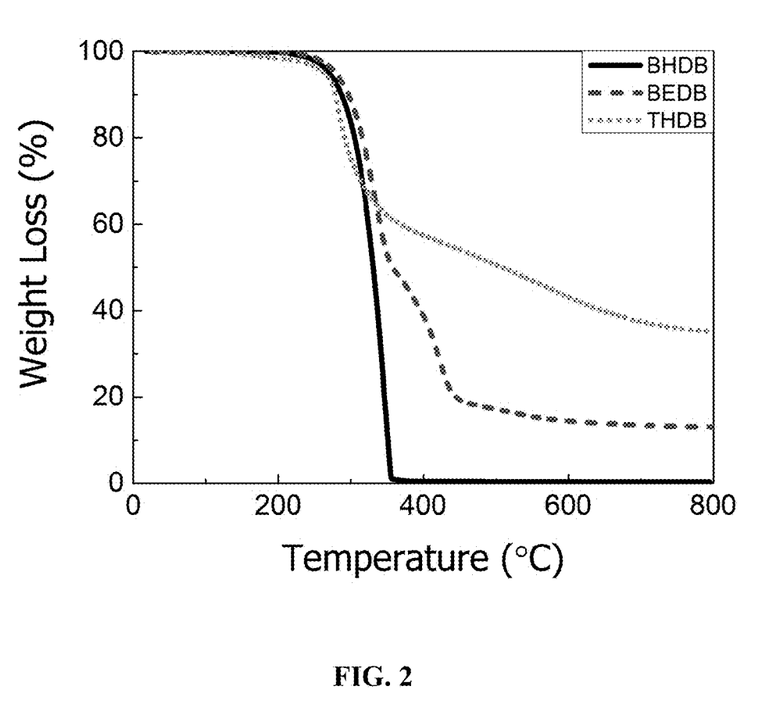
FIG. 2. Exemplary thermogravimetric analysis (TGA) curves for BHDB, BEDB, and THDB.

Thermal properties of BHDB and THDB, analyzed separately by thermogravimetric analysis (TGA), differ greatly. The TGA curves of FIG. 2 show that BHDB volatilizes completely at ~350° C., while THDB produces a substantial amount of char residue (~40% at 800° C.

Figure 3:
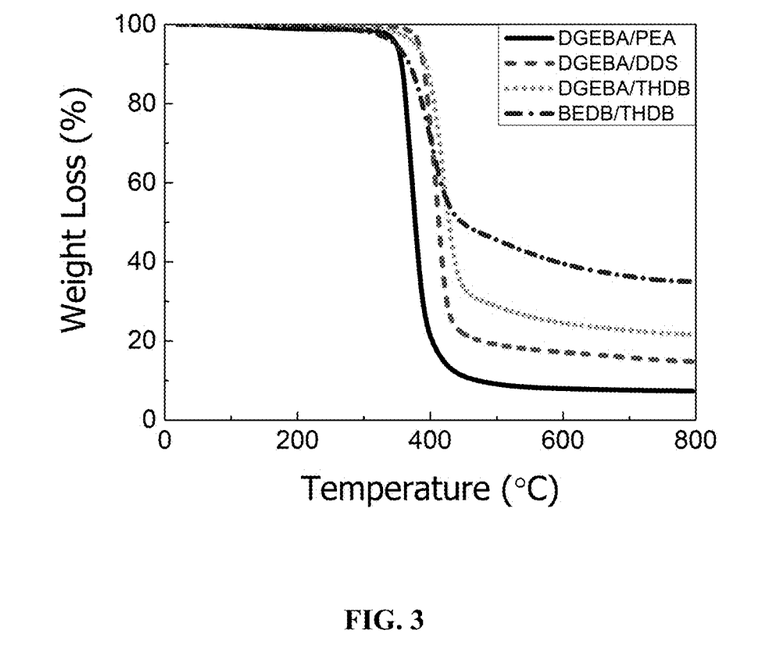
FIG. 3. Exemplary TGA analysis of THDB-containing resins vs. BPA-based structures.
Figure 4:
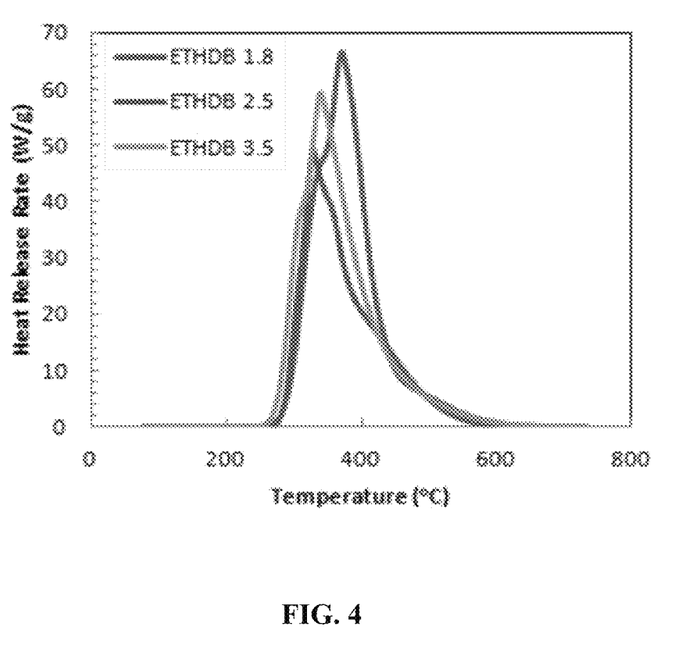
FIG. 4. Exemplary heat release rate curves of different epoxy numbers of ETHDB 1.8, 2.5, and 3.5.
Figure 5:
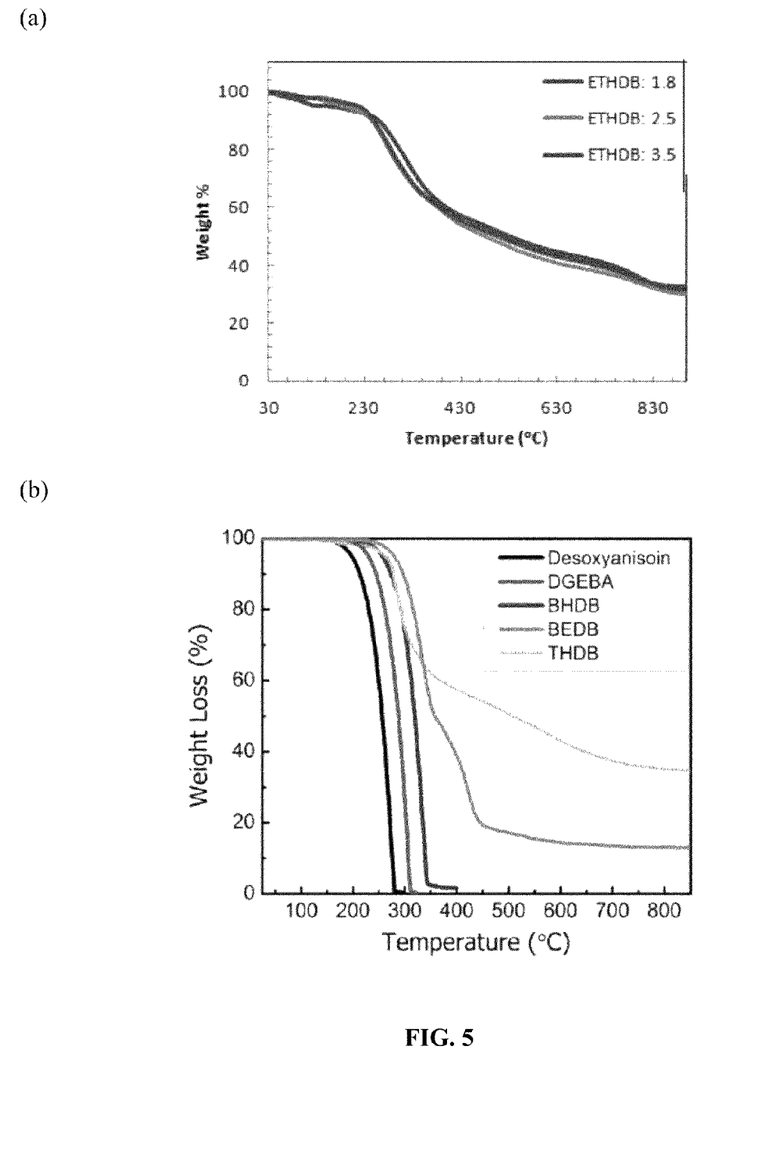

The multifunctional structure of THDB makes it well-suited for integration into polymer materials as a cross-linker, as tested here in epoxy curing and subsequent evaluation of mechanical and thermal properties. TGA thermograms of epoxy resins with and without deoxybenzoin integrated into the network are shown in FIG. 3, with clear differences arising from the presence of THDB in the cured material. For example, resins prepared from the diglycidyl ether of BPA (DGEBA) by curing with polyetheramine (PEA) displayed almost no char residue beyond 450° C. However, replacement of PEA with THDB gave epoxy polymers with a char residue of 22%. The all-deoxybenzoin cured system, prepared from THDB and BEDB, produced nearly 40% char at 800° C., approximately 3 times that of a conventional DGEBA/DDS system (char yield ~15%). Pyrolysis combustion flow calorimetry (PCFC) revealed that the heat release capacity (HRC) and total heat release (THR) values decreased significantly due to the inclusion of deoxybenzoin monomers (defining HRC as the maximum heat released divided by the heating rate).

Describing these systems in terms of HRC eliminates reliance on heating rate that is typical of standard flammability measurements (i.e. heat release rate), rendering it a material dependent property. THR is the total heat of complete combustion of the pyrolysis products per mass of sample used in the measurement. Lower HRC and THR values are thus good indicators of increasing the flame retarding property of the polymer. For instance, by incorporating deoxybenzoin into the resins, the measured HRC of BEDB resins cured with PEA was 480 J/g-K, nearly a 50% reduction from that of DGEBA (850 J/g-K) (Table 1). Introducing THDB into DGEBA resins led to further reduction in HRC, to 393 J/g-K, demonstrating (1) the beneficial

TABLE 1

Thermal Characteristics of Deoxybenzoin-based Epoxy Resins

| Formulation | HRC (J/K-g) | THR (kJ/g) | $T_g$ (° C.) | $T_d$ (° C.) 5% weight loss | Residue % |
| --- | --- | --- | --- | --- | --- |
| DGEBA/PEA | 850 | 29 | 89 | 349 | 7 |
| DGEBA/DDS | 510 | 26 | 219 | 383 | 15 |
| DGEBA/THDB | 393 | 20 | 164 | 378 | 22 |
| BEDB/THDB | 229 | 13 | 110 | 322 | 34 |

$T_g$ values obtained from DSC. $T_d$ and residue percent from TGA. HRC and THR acquired on MCC. PEA refers to polyetheramine, Jeffamine D230.

effect of deoxybenzoin monomers for tempering heat release, and (2) their facile integration into curing chemistry with conventional epoxies.

The all-deoxybenzoin cross-linked resins displayed by far the most favorable heat release properties, with THR and HRC values measured as 13 kJ/g and 229 J/g-K, respectively. These values are almost half that of any of the resins previously reported from BEDB with conventional cross-linking structures: for example, BEDB cross-linked with DDS gave THR and HRC values of 17.2 kJ/g and 420 J/g-K. (Ryu, et al. 2009 *Polymer* 50(3):767-774.) While these values could be lowered further by inclusion of halogenated or inorganic flame retardant additives, these deoxybenzoin systems possess favorable thermal properties in the absence of additives of any sort.

The adhesive materials from THDB and BEDB resins proved to have suitable mechanical properties to be considered for any of a variety of adhesive applications, while the flammability properties of the materials obtained were substantially lower than conventional systems, even in the absence of anti-flammable additives.

In one aspect, the invention generally relates to a compound having the structural formula of:

wherein each R in (OR)$_i$ and (OR)$_j$ is independently selected from H and i is an integer selected from 1, 2, 3, 4 and 5; j is an integer selected from 1 and 2; and each of R$_1$ and R$_2$ is independently selected from H and (C$_1$-C$_6$) alkyl groups.

In certain embodiments, i is 2 or 3, j is 1. In certain embodiments, wherein each of $R_1$ and $R_2$ is H.

In certain preferred embodiments, the compound has the structural formula of:

wherein each R independently is H or

In certain preferred embodiments, each R is H. In certain preferred embodiments, at least one R is

In certain preferred embodiments, each R is

In another aspect, the invention generally relates to a polymer prepared from a monomer having the structural formula of wherein each R in $(OR)_i$ and $(OR)_j$ is independently selected from H and i is an integer selected from 1, 2, 3, 4 and 5; j is an integer selected from 1 and 2; and each of $R_1$ and $R_2$ is independently selected from H and ($C_1$-$C_6$) alkyl groups.

In certain embodiments, i is 2 or 3, j is 1. In certain embodiments, each of $R_1$ and $R_2$ is H.

In certain preferred embodiments, the polymer is prepared from a monomer having the structural formula of wherein each R independently is H or

In certain preferred embodiments, each R is H. In certain preferred embodiments, at least one R is

In certain preferred embodiments, each R is

In yet another embodiment, the invention generally relates to a minimal- or non-flammable composition, which includes a polymer comprising a monomer having the structural formula of wherein each R in $(OR)_i$ and $(OR)_j$ is independently selected from H and i is an integer selected from 1, 2, 3, 4 and 5; j is an integer selected from 1 and 2; and each of $R_1$ and $R_2$ is independently selected from H and ($C_1$-$C_6$) alkyl groups.

In certain embodiments, i is 2 or 3, j is 1. In certain embodiments, each of $R_1$ and $R_2$ is H.

In certain preferred embodiments, the monomer has the structural formula of wherein each R independently is H or

In certain preferred embodiments, each R is H. In certain preferred embodiments, at least one R is In certain preferred embodiments, each R is

EXAMPLES

Materials

Phloroglucinol, 4-hydroyphenyl-acetonitrile, aluminum chloride, anhydrous ethyl ether, calcium chloride, hydrochloric acid, epichlrohydrin, potassium carbonate, and dimethyl formamide, tetrabutylammonium bromide, and isopropanol were purchased from Aldrich Chemical Company. Methanol, acetone, and sodium hydroxide were purchased from Fisher Scientific. The purchased chemicals were used as received unless otherwise noted.

Characterization

Nuclear magnetic resonance (NMR) spectra were obtained on a Bruker DPX300 or Avance 400 spectrometer. Thermogravimetric analysis (TGA) was performed under nitrogen on a Q500 (TA Instruments) at a heating rate of 10° C./min. Char yields were determined by TGA, taken from the mass residue at 800° C. Differential scanning calorimetry (DSC) was performed on a Q200 (TA Instruments) with a heating rate of 10° C./min. Specific heat release rate (HRR, W/g), heat release capacity (HRC, J/(g-K)), and total heat release (THR, kJ/g) were measured on a microscale combustion calorimeter (MCC). MCC operates as a pyrolysis combustion flow calorimeter (PCFC), and was conducted from 80 to 750° C. at a heating rate of 1° C./s in an 80 cm³/min stream of nitrogen. The anaerobic thermal degradation products in the nitrogen gas stream were mixed with a 20 cm³/min stream of oxygen prior to entering the combustion furnace (900° C.). Heat release is quantified by standard oxygen consumption methods typical to PCFC. (Lyon, et al. 2004 *J Anal Appl Pyrol* 71(1):27-46; ASTM. Standard Test Method for Determining Flammability Characteristics of Plastics and Other Solid Materials Using Microscale Combustion calorimetry. ASTM D7309-13. West Conshohocken, PA: ASTM International, 2013. pp. 11.) During the test, HRR is obtained from dQ/dt at each time interval, taking into account the initial sample mass (~5 mg). The HRC is obtained by dividing the maximum HRR by the heating rate.

Synthesis of diglycidyl ether of 4,4'-bishydroxydeoxybenzoin (BEDB)

BHDB (68.0 g, 296 mmol) was added to a round-bottom flask with epichlorohydrin (232 mL, 2.96 mol) isopropanol (115 mL) and water (23 mL). A 20% NaOH solution (23.0 g NaOH in 115 mL water) was added dropwise at 65° C. and allowed to react for a total of 1.5 hours from the first addition of base. The reaction was cooled and chloroform was added to extract the product. After several washings with water and brine, the organic layer was dried over magnesium sulfate. The product was subsequently poured into hexane, precipitating 79.0 g of the final diglycidyl ether product (80% yield). $M_p$ 105° C. $^1$H NMR (DMSO-d6, ppm): 8.01 (d, 2H, J=8.0 Hz, Ar—H), 7.20 (d, 2H, J=7.8 Hz, Ar—H), 6.97 (d, 2H, J=7.8 Hz, Ar—H), 6.90 (d, 2H, J=6.9 Hz, Ar—H), 4.38-4.16 (m, 2H, —O—CH$_2$-oxirane), 4.16 (s, 2H, Ar—CH2-CO—Ar), 4.07-3.92 (m, 2H, —O—CH$_2$-oxirane), 3.45-3.31(m, 2H, 2 (oxirane CH)), 3.01-2.89 (m, 2H, 2(oxirane CH$_2$)), 2.84-2.74 (m, 2H, 2 (oxirane CH$_2$)). $^{13}$C NMR (CDCl$_3$, ppm): 196.5, 162.3, 157.4, 130.9, 130.5, 130.0, 127.5, 114.9, 114.4, 68.9, 66.8, 50.1, 49.9, 44.7, 44.6, 44.4.

Synthesis of 2,4,4',6 tetrahydroxydeoxybenzoin (THDB)

Phloroglucinol (39.5 g, 313 mmol), 4-hydroxyphenylacetonitrile (50.0 g, 376 mmol) and anhydrous ethyl ether (200 mL) were added to a roundbottom flask. Under a nitrogen atmosphere at 0° C., aluminum chloride (5.00 g, 39.3 mmol) was added and the flask was capped quickly. A steady stream of HCl$_{(g)}$, generated by addition of concentrated HCl$_{(l)}$ over calcium chloride, was piped into the mixture. This was continued for 6 hours, yielding a pink precipitate. The precipitate was kept overnight at 0° C., then filtered and refluxed in water (500 mL) for 2 hours. This produced a light red powder that was isolated by filtration and dried. The powder was dissolved in acetone and charged with charcoal to afford 42.9 g of pale yellow powder (54% yield). $M_p$ 259° C. $^1$H NMR (DMSO-d6, ppm): 12.27 (s, 2H,2,6-OH), 10.41 (s, 1H, 4-OH), 9.23 (s, 1H, 4'-OH), 7.02 (d, 2H, J=8.1 Hz, H-2',6'), 6.68 (d, 2H, J=8.1 Hz, H-3',5'), 5.82 (s, 2H, H-3,5), 4.21(s, 2H, Ar—CH$_2$—CO—Ar). $^{13}$C NMR (DMSO-d6, ppm): 203.5, 165.2, 164.7, 156.31, 131.0, 126.4, 115.4, 104.1, 95.2, 48.5.

Preparation of BEDB/THDB Resins

Cross-linked resins were prepared in a stoichiometric ratio of BEDB to THDB (2 mol BEDB: 1 mol THDB). As the melting points of the two monomers differ by 150° C., the higher melting point THDB was solubilized in methanol prior to cross-linking BEDB was melted at 150° C. and the THDB solution was added slowly while stirring. The resin was quickly poured into a mold and cured overnight at 200° C. Teflon molds were used for fracture toughness specimens and Surfasil-treated test tubes were used for compression samples. Comparative samples were prepared by reacting the diglycidyl ether of bisphenol A (DGEBA, D.E.R.332, from Dow Chemical Company) with stoichiometric amounts of polyetheramine (PEA, Jeffamine D230, Huntsman), 4,4'-diaminodiphenylsulfone (DDS, Acros Organic), and THDB (2 glycidyl ether:1 crosslinker). DGEBA and PEA were cured at 80° C. for 3 hours, then at 120° C. for 3 hours; DGEBA with DDS was cured at 200° C. for 4 hours then at 220° C. for 2 hours. Cross-linked resins of DGEBA with THDB were prepared in identical fashion as for the BEDB/THDB case.

epoxies display low heat release capacities of 208 to 166 J/g-K and total heat release values of 13 and 11 kJ/g.

TABLE 2

Thermal properties of epoxy resins prepared from ETHDB-3.0

| Sample | HRC (J/g-K) | THR (kJ/g) | $T_d$ (° C.) | % Char |
|---|---|---|---|---|
| E-THDB-3.0/DDM | 208 | 13 | 357 | 35 |
| E-THDB-3.0/DDS | 166 | 11 | 376 | 35 |

ETHDB-3.0

ETHDB-4.0 (TEDB)

Synthesis of ETHDB-3.0

THDB (20.8 g, 80 mmol) was mixed with epichlorohyrin (100 mL) with phase transfer catalyst, tetrabutylammonium bromide (TBAB) (1.26 g, 4 mmol), and heated to reflux for one hour in order to solubilize THDB. After returning to room temperature, a solution of NaOH (20%, 25.6 g in 126 mL water) with additional TBAB (1.26 g, 4 mmol) was added dropwise and allowed to react at room temperature for 1.25 hours. The solution was then extracted into ethyl acetate, washed with water (3×) and brine (3×), and dried over magnesium sulfate. After removal of solvent, the material was purified by column chromatography (19:1 DCM:EtOAc) yielding 6.48 g (19.6% yield). m.p.=72-75° C. $^1$H NMR (DMSO-d6): 13.22 (s, 1H, 2-OH), 7.15 (d, 2H, J=8.9 Hz, H-2',6'), 6.89 (d, 2H, J=8.9 Hz, H-3',5'), 6.2 (d, 1H, J=3.0 Hz, H-3), 6.13 (d, 1H, J=3.0 Hz, H-5), 4.52-4.37 (m, 2H, —O—CH$_2$-oxirane), 4.34-4.20 (m, 1H, —O—CH$_2$-oxirane), 4.29 (s, 2H, Ar—CH$_2$—CO—Ar), 3.99-3.72 (m, 3H, —O—CH$_2$-oxirane), 3.46-3.28 (m, oxirane CH), 2.91-2.81 (m, oxirane-CH$_2$), 2.76-2.67 (m, oxirane-CH$_2$). $^{13}$C NMR (DMSO-d6): 203.4, 165.6, 164.7, 161.4, 157.4, 131.3, 128.1, 114.7, 106.6, 95.3, 92.6, 70.9, 69.9, 69.4, 50.2, 49.8, 49.2, 44.4, 44.2. MS (ESI) m/z=451.13 (M+Na)$^-$, 429.15 (M+H)$^+$.

Thermal Properties of ETHDB-3.0 Resins

Epoxy resins were prepared by reacting ETHDB-3.0 with aromatic diamine cross-linkers, 4,4'-diaminodiphenylsulfone (DDS) and 4,4'-diaminodiphenylmethane (DDM). ETHDB-3.0 was melted at 100° C. and then stoichiometric amounts of cross-linker were added. The mixture was further cured by reacting at 150° C. followed by an additional 5 hours of curing at 200° C. Preliminary results from cross-linked ETHDB

Synthesis of ETHDB-4.0 (TEDB)

THDB (2.0 g, 7.6 mmol) and potassium carbonate (6.63 g, 47.9 mmol) were combined in a flask with DMF (10 mL) and acetone (10 mL). An excess of epichlorohydrin (12.5 mL, 159 mmol) was added and the mixture was heated at 70° C. overnight. Water was added to quench the reaction, the products were separated into ethyl acetate, washed with water and brine (3× each). After drying over magnesium sulfate, filtration, and solvent removal, the product was purified by column chromatography (9:1 DCM: EtOAc). This yielded 700 mg (20% yield) of viscous yellow oil. $^1$H NMR (DMSO-d6): 7.09 (d, 2H, J=9.0 Hz, H-2',6'), 6.87 (d, 2H, J=9.0 Hz, H-3',5'), 6.32 (s, 2H, H-3,5), 4.39-4.24 (m, 4H, —O—CH$_2$-oxirane), 3.93 (s, 2H, Ar—CH$_2$—CO—Ar), 3.90-3.74 (m, 4H, —O—CH$_2$-oxirane), 3.39-3.23 (m, oxirane CH), 2.90-2.79 (m, oxirane-CH$_2$), 2.74-2.62 (m, oxirane-CH$_2$). $^{13}$C NMR (DMSO-d6): 200.8, 161.0, 157.4, 156.7, 131.3, 127.4, 114.6, 113.7, 93.4, 69.9, 69.8, 69.4, 50.4, 50.2, 50.0, 44.2, 44.1. MS (ESI) m/z=507.15 (M+Na)$^+$, 485.2 (M+H)$^+$.

THDB

-continued

TEDB

Heat Release Properties

As a monomer, THDB showed favorable heat release properties relative to previously reported data concerning other deoxybenzoin derivatives. BHDB itself sublimes, yielding oil char at 350° C. However, TGA analysis showed that THDB had a char yield on average of 35% under nitrogen atmosphere. Also the HRC and THR are lower than that of the BEDB, dropping from 260 J/g-K to 103 J/g-K and 15.8 kJ/g to 7.9 kJ/g respectively. The epoxy analogs of THDB further show a decrease in heat release capacities, from 54-83 J/g-K, and total heat release from 4.6-6.2 kJ/g.

TABLE 3

Thermal Properties of Synthesized Monomers

| | HRC (J/g-K) | Total HR (kJ/g) | HRR (W/g) | Residue Yield % |
|---|---|---|---|---|
| BEDB | 260 | 20 | 243 | 24 |
| THDB | 103 | 8 | 76 | 31 |
| ETHDB 1.8 | 68 | 5.6 | 68 | 31 |
| ETHDB 2.5 | 69 | 5.7 | 57 | 30 |
| ETHDB 3.5 | 64 | 6.2 | 64 | 33 |

Thus, novel deoxybenzoin derivatives were synthesized that are useful in halogen-free flame resistant applications. The HRC and HRR values found for THDB and E-THDB mixtures showed improvement over BHDB and BEDB derivatives. Moreover, even unfunctionalized THDB exhibited promising thermal results in resin mixtures, and can provide a benchmark for novel cured resins with E-THDB.

It is noted that reacting THDB with epichlorohydrin under basic conditions affords epoxide-substituted compounds, typically in which 2, 3 or 4 of the hydroxyl groups are substituted with an epoxide, a THDB epoxy derivative having only one epoxide group can be prepared. In a typical reaction sequence, THDB is reacted with an excess of epichlorohydrin to give a product with some average number of epoxides per molecule (described as the "epoxy number"). The epoxy number is determined experimentally by nuclear magnetic resonance spectroscopy, and can be any number greater than zero and less than or equal to four. In Practice, epoxy numbers greater than one and up to four can be useful towards using the epoxide products in adhesive formulations. In the exemplary embodiment shown here, with four epoxide groups is referred to as TEDB, or tetraepoxydeoxybenzoin.

Each R independently = H or

The compounds and materials, along with the synthetic methodologies disclosed herein can have broad impact on such diverse fields of fabricating textiles, upholstery, construction materials, various air, land or sea vehicles, and microelectronic devices and appliances.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

Incorporation by Reference

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

Equivalents

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. A compound having the structural formula of:

wherein
each R in $(OR)_i$ and $(OR)_j$ is independently selected from H and

;

i is an integer selected from 2, 3, 4 and 5;
j is an integer selected from 1 and 2; and
each of $R_1$ and $R_2$ is independently selected from H and $(C_1\text{-}C_6)$ alkyl groups,
wherein at least one R in $(OR)_i$ and $(OR)_j$ is.

.

2. The compound of claim 1, wherein i is 2 or 3, j is 1.

3. The compound of claim 2, wherein each of $R_1$ and $R_2$ is H.

4. The compound of claim 3, having the structural formula of:

wherein each R independently is H or and at least one R is

.

5. The compound of claim 4, wherein each R is

.

6. A polymer prepared from a monomer having the structural formula of wherein
each R in $(OR)_i$ and $(OR)_j$ is independently selected from H and

;

i is an integer selected from 2, 3, 4 and 5;
j is an integer selected from 1 and 2; and
each of $R_1$ and $R_2$ is independently selected from H and $(C_1\text{-}C_6)$ alkyl groups, wherein at least one R in $(OR)_i$ and $(OR)_j$ is

.

7. The polymer of claim 6, wherein i is 2 or 3, j is 1.

8. The polymer of claim 7, wherein each of $R_1$ and $R_2$ is H.

9. The polymer of claim 8, prepared from a monomer having the structural formula of wherein each R independently is H or and at least one R is

.

10. The polymer of claim 9, wherein each R is H.

11. The polymer of claim 9, wherein at least one R is

12. The polymer of claim 9, wherein each R is

13. A non-flammable composition comprising a polymer comprising a monomer having the structural formula of wherein
 each R in $(OR)_i$ and $(OR)_j$ is independently selected from H and i is an integer selected from 2, 3, 4 and 5;
j is an integer selected from 1 and 2; and
each of $R_1$ and $R_2$ is independently selected from H and $(C_1\text{-}C_6)$ alkyl groups.

14. The non-flammable composition of claim 13, wherein i is 2 or 3, j is 1.

15. The non-flammable composition of claim 14, wherein each of $R_1$ and $R_2$ is H.

16. The non-flammable composition of claim 15, wherein the monomer has the structural formula of wherein each R independently is H or and at least one R is

17. The non-flammable composition of claim 13, wherein at least one R is

18. The non-flammable composition of claim 13, wherein each R is

* * * * *